United States Patent [19]

Buzzard

[11] Patent Number: 4,916,954

[45] Date of Patent: Apr. 17, 1990

[54] FATIGUE TESTING APPARATUS

[75] Inventor: Robert J. Buzzard, Berea, Ohio

[73] Assignee: The United States of America as represented by the United States National Aeronautics and Space Administration, Washington, D.C.

[21] Appl. No.: 396,263

[22] Filed: Aug. 21, 1989

[51] Int. Cl.$^4$ .............................................. G01N 3/32
[52] U.S. Cl. ........................................ 73/799; 73/845
[58] Field of Search ................ 73/799, 845, 841, 846, 73/831, 834, 835, 810, 815

[56] References Cited

U.S. PATENT DOCUMENTS

| | | | |
|---|---|---|---|
| 2,812,658 | 11/1957 | Damm et al. | 73/103 |
| 3,127,765 | 4/1964 | O'Neil | 73/94 |
| 3,406,567 | 10/1968 | Terry | 73/101 |
| 3,566,681 | 3/1971 | Iosipescu et al. | 73/101 |
| 4,409,481 | 10/1983 | Archer | 73/762 |

FOREIGN PATENT DOCUMENTS 646768 10/1962 Italy.
1259135 9/1986 U.S.S.R. ............................... 73/799

Primary Examiner—Jerry W. Myracle
Attorney, Agent, or Firm—Gene E. Shook; John R. Manning; James A. Mackin

[57] ABSTRACT

Apparatus is provided for obtaining a single crack in fatigue loading which emanates from a predetermined starting notch in a test specimen. This crack propagates in a direction in line with that of the applied Mode II load. The loading may be performed either monotonically or in a cyclic fatigue.

20 Claims, 3 Drawing Sheets

FATIGUE TESTING APPARATUS

ORIGIN OF THE INVENTION

The invention described herein was made by an employee of the United States Government and may be manufactured and used by or for the Government for governmental purposes without the payment of any royalties thereon of therefor.

TECHNICAL FIELD

This invention is concerned with the testing of materials under Mode II loading. While the invention is particularly directed to such testing in cyclic fatigue, it may be used in monotonic loading to fracture.

Mode II refers to edge sliding mode of failure or crack propagation in a material while Mode I refers to the opening mode of displacement in which the crack surfaces move directly apart. Naturally occurring failures of structures are rarely attributable to purely Mode II loading but rather to a combination of Mode II and Mode I. However, knowledge of the strength or fatigue characteristics of materials under Mode II loading is desirable in structural analysis individually and as a separate constituent in loading combinations. Such knowledge is particularly important in understanding the phenomena associated with mixed mode fatigue failures in high performance aircraft engine bearing races.

Various methods have been proposed to achieve a purely Mode II failure in a test specimen. While some of these prior art procedures claim to transmit a Mode II loading to a specimen upon initial loading, in practice further loading may cause failure at locations other than the intended test zone, or may distort the test configuration to such an extent that failure occurs by mechanisms other than Mode II. Also, failure may initiate at more than one location thereby making analysis of the test data difficult.

It is, therefore, an object of the present invention to provide an apparatus for obtaining a crack in fatigue loading which propagates in a direction in line with that of an applied Mode II load.

A further object of the invention is to provide material testing apparatus having a specimen which features a single crack emanating from a predetermined starting notch.

BACKGROUND ART

Terry U.S. Pat. No. 3,406,567 describes a portable shear test device that is used for testing bulk material, such as snow and soil. Iosipescu et al U.S. Pat. No. 3,566,681 is concerned with shear testing of rocks and other building materials.

Archer U.S. Pat. No. 4,409,841 is directed to a fatigue damage indicator having four holes in a test plate which provide four zones of crack initiation. Damm et al U.S. Pat. No. 2,812,658 sets out a method of fatigue testing hooks.

DISCLOSURE OF THE INVENTION

Apparatus constructed in accordance with the present invention facilitates testing of materials under Mode II loading. This test loading may be performed either monotonically or preferably in cyclic fatigue.

A single crack is produced which emanates from a predetermined starting notch. This crack propagates in a direction in line with that of the applied Mode II load in most engineering type materials.

BRIEF DESCRIPTION OF THE DRAWINGS

The objects, advantages, and novel features of the invention will be more fully apparent from the following detailed description when read in connection with the accompanying drawings wherein.

BEST MODE FOR CARRYING OUT THE INVENTION

Figure 1:
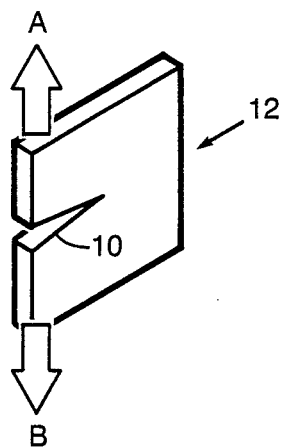
FIGS. 1, 2, and 3 illustrate the basic mode of crack extension with Mode I being shown in FIG. 1, Mode II in FIG. 2, and Mode III in FIG. 3.
Figure 2:
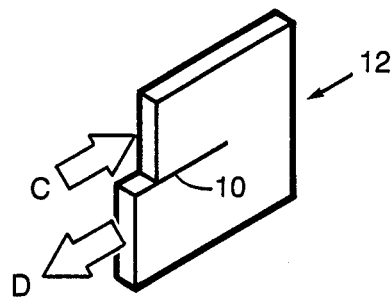
Figure 3:
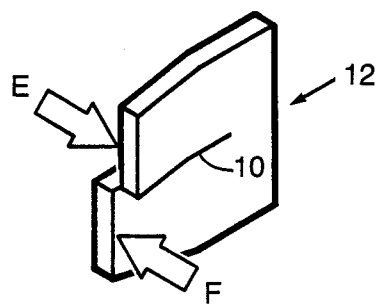

Referring now to the drawings, FIGS. 1, 2, and 3 show the three types of loading. Mode I is shown in FIG. 1 wherein opposed forces along the same axis illustrated by the arrows A and B tend to open a groove 10 in a test specimen 12.

Mode II refers to an edge sliding mode of failure or crack propagation in a material and is illustrated by the arrows C and D where forces are applied in opposite directions to portions of the test specimen 12 on either side of the groove 10. The forces C and D are parallel to the groove 10 and perpendicular to the edge of the specimen 12.

In Mode III loading a pair of parallel forces illustrated by the arrows E and F in opposite directions are likewise applied to portions of the test specimen 12 on either side of the groove 10. However, the forces E and F are perpendicular to the faces of the specimen 12.

Naturally occurring failures of structures are rarely attributable to loading forces acting in only one of the idealized directions depicted in FIGS. 1 to 3, but rather to a combination of two or all three modes simultaneously. In order to gain insight into crack behavior under these combined loading conditions, an understanding of the strength or fatigue characteristics of materials under each individual loading condition is imperative. Knowledge of the strength of fatigue characteristics of materials under Mode II loading is obtained by using the present invention.

Various prior art procedures have been proposed in an attempt to achieve purely Mode II failure on a test specimen. While some of these procedures claim to transmit Mode II loading to a specimen upon loading, in practice further loading causes distortion of the test configuration to such an extent that failure finally occurs by mechanisms other than Mode II. Such distortions may ultimately introduce bending stresses in the test zone which produce mixed Mode II-Mode I failures.

In most methods the best obtainable crack for any material is one that emanates at an angle of about 70° from the direction of load application at the starter notch tip. Elastic analyses indicate that a Mode II fatigue crack should propagate in the 70° direction. However, if a crack actually develops and propagates in that direction then the loading configuration becomes distorted to a situation wherein a mixed Mode I-Mode II condition exists. If the crack continues to grow in that direction, Mode I will predominate until finally the Mode II condition will no longer exist.

A specimen configuration and loading condition are preferred wherein a Mode II load will cause crack growth in a plane which is in-line with the load and will remain in-line throughout the duration of the test. Furthermore, it is highly desirable that the test specimen be provided with a single starter notch as opposed to a double-end notch or a pair of single tip notches. This facilitates the obtaining of crack propagation data and precludes the possibility of an imbalance in loading conditions brought on by a mismatch in crack length. The specimen design should be amenable to numerical analysis methods so that the test data may be expressed in engineering terms.

Figure 4:
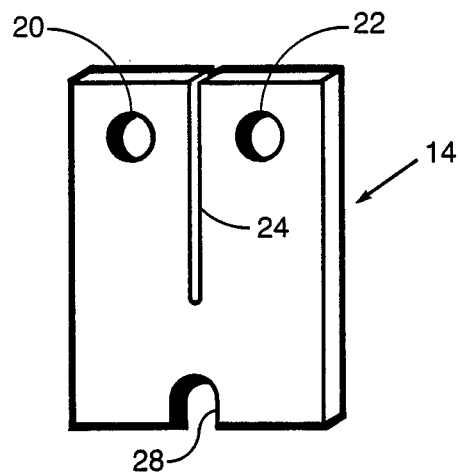
FIG. 4 is a perspective view of a Mode II test specimen constructed in accordance with the present invention.
Figure 5:
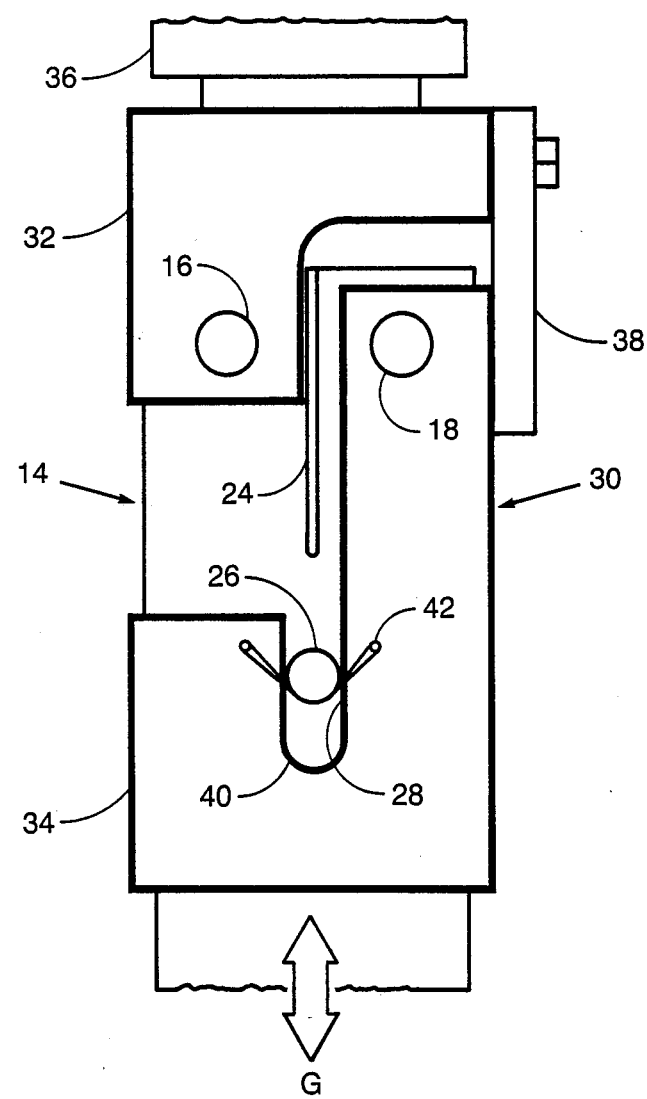
FIG. 5 is an elevation view of a testing fixture constructed in accordance with the present invention to apply alternating loads.

A test specimen 14 constructed in accordance with the present invention is shown in FIGS. 4 and 5. To provide for loading, close fitting hardened steel pins 16 and 18 are inserted into mating major loading holes 20 and 22 on opposite sides of a central notch or slot 24 which extends from one edge of the test specimen 14. The pin 16 engages the hole 20 while the pin 18 engages the hole 22. A similar steel pin 26 mates with a full cutout 28 at the opposite end of the specimen 14.

Should photoelastic fringe patterns be desired to ascertain the type of alignment of the loading forces at the notch tip, the test specimen 14 may be fabricated from a plate of commercially available polymethylmethacrylate or from commercial resin. Metallic specimens 14, machined from various enginerring type materials fulfill the main purpose of this invention.

The length of the notch or slot 24 as referenced from the midpoint of a common centerline of the major loading holes 20 and 22 to the root of notch 24 may vary. The ratio of this length to the vertical distance along the notch 24 from this same centerline of the holes 20 and 22 and the top of the cutout 28 is between 0.6 and 0.75. This ratio ensures optimization of the Mode II component in the test zone. In a strict sense a "pure" Mode II condition will not exist at extreme ratios of these distances because a very small Mode I loading is present. However, when the ratio is between 0.6 and 0.75 the Mode I component is so small as to be essentially nonexistent.

The assembly is placed into a testing fixture 30 as shown in FIG. 5. The fixture 30 has two sections in the form of an upper clevis 32 that is fixed and a lower clevis 34 that is movable as illustrated by the arrow G. Each clevis has a centrally disposed slot to accommodate the specimen 14, and the pins 16 and 18 are mounted in suitable apertures in the clevises.

The fixture 30 is secured to a suitable test machine in a conventional manner so that the central axis of loading passes through the center line of the notch or groove 24 and the axis of the lower pin 26. The loading is recorded by a load cell 36 in a conventional manner.

Compression loading of the testing fixture 30, as shown by the upward direction of the arrow G, transmits a downward force to the left side of the test specimen 14 through the pin 16. Likewise, an upward force is transmitted to the right side of the specimen through the pin 18. These forces result in a counterclockwise rotational moment in the specimen 14. This moment is arrested as the pin 26 presses against the vertical leg of the lower clevis 34. The major loading forces are thusly directed in opposing vertical directions which have as a demarcation the central loading axis of the specimen. The balanced alignment of the direction of these forces has been verified by photoelastic methods. Such alignment remains stable at loads approaching fracture of the specimen.

Increasing the load on the system causes the righthand, or tensile, leg of the specimen 14 to move upward relative to the other half of the specimen. In materials which can tolerate such relative displacement, which includes many structural and enginerring materials, a crack will propagate in the Mode II direction along the loading centerline. Under cyclic loading conditions, crack progression may be measured optically or by other suitable means, and useful Mode II fatigue data may be generated.

In materials which are not capable of exhibiting relative displacements along the loading centerline as a result of the described loading condition, which includes very brittle materials, the specimen fails across the tensile leg with the failure originating at the notch tip and progressing at approximately a 70° angle. Various methods have been employed which set forth rationale to describe such behavior analytically. While fracture of this nature is not the primary goal of this invention, it nevertheless can be used to provide a sense of mixed Mode I and II data useful to the engineering community.

Depending upon the rigidity of the system and loads required to perform a test, a backup plate 38 may be utilized to reduce sideward movement of the fixture as a result of its arresting the rotational moment. A roller or a thin brass spacer (not shown) may be placed between the plate 38 and the opposing face of the test fixture 30 to protect the fixture from abrading against the backup plate 38 should prolonged fatigue cycling at high loads be required.

If it is so required, the direction of the applied Mode II loading force may be reversed by moving the lower clevis 34 in the opposite direction as indicated by the downward direction of the arrow G. Inasmuch as a symmetrical specimen is used, the full cutout 28 at the pin 26 enables either leg of the specimen 14 to move vertically past the pin 26.

The lower clevis 34 is slotted at 40 to provide lateral support and thereby arrest rotational moments in the specimen under Mode II loads applied in either the tensile or compressive directions G. A spring type pin support 42 retains the lower pin 26 in place relative to the specimen 14.

ALTERNATE EMBODIMENT OF THE INVENTION

While the preferred embodiment of the invention has been shown and described it will be appreciated that various structural modifications may be made to the apparatus without departing from the spirit of the invention. Such an embodiment is the use of this invention, with slight modification, to introduce a predetermined amount of Mode I opening of the notch 24 while also applying the Mode II loading in the previously described manner. For example, Mode I opening may be accomplished by increasing the distance between the major loading holes of the test apparatus which receive the pins 16 and 18 while keeping the distance initially wedging the specimen 14 open to install it into the test apparatus.

Figure 6:
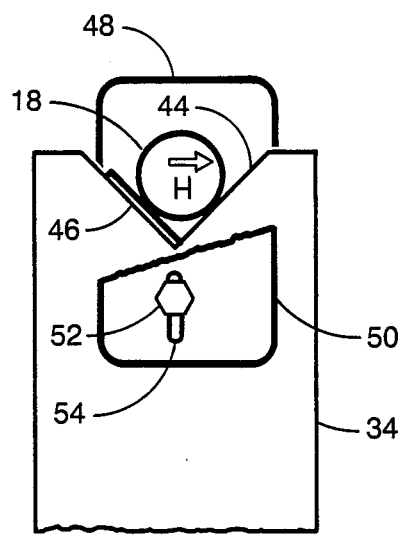
FIG. 6 is an elevation view of a portion of a testing fixture which incorporates an alternate embodiment of the invention.

An alternative method of applying the opening displacement is to replace the loading hole in the clevis 34 that receives the pin 18 with an open vee-shaped notch 44 upon which the loading pin 18 is supported as shown in FIG. 6. The effective distance between the loading pins 16 and 18 may be altered by inserting thin shims 46 between the loading pin and the inclined face of the vee notch 44. This causes the loading pin 18 to be displaced horizontally as indicated by the arrow H when a compressive load is applied to the test fixture thereby resulting in a controlled opening of the specimen notch 24.

The amount of opening is accurately measured along the common centerline of the major loading pins 16 and 18 at the outer edges of the specimen 14. The load at the tip of the notch 24 is determined from knowledge of this opening displacement and an experimentally determined relationship describing such opening as a function of the applied Mode I load. The motion of the loading pin 18 is arrested when sufficient load is applied to the system as to cause the loading pin 18 to come to rest against the opposing face of the vee-notch 44. This enables the opening displacement to remain fixed during the subsequent application of Mode II loads, thereby maintaining a constant Mode I loading. This feature is very significant toward the acquisition of meaningful mixed mode test data.

It is recognized that by using an open vee-notch in place of the fully circular shaped hole at 18 the fixture can then only be operated in the compressive mode. However, the reverse loading feature can be restored by the addition of support arms 48 and 50 to both sides of the lower clevis 34. The arms 48 and 50 contain a hole which engages the loading pin 18 while the apparatus is under sufficient load to cause the desired amount of Mode I opening to occur.

The support arms 48 and 50 are anchored to the upright vee-notch. Anchoring may be accomplished by use of machine screw 52 passing through a slotted hole 54 in the arm 50 and into a threaded hole in the clevis 34. The slotted design allows for adjustment of the location of the loading pin 18 to accommodate various amounts of opening in the Mode I direction. Alternate compressive and tensile loads may now be applied to the apparatus.

Various other modifications may be made without departing from the scope of the subjoined claims.

I claim:

1. Apparatus for testing materials under Mode II loading wherein the material being tested is in the form of a plate having a pair of spaced loading holes with a centrally disposed notch extending from one edge between said holes toward a full cutout in the opposite edge thereof comprising
   a fixed clevis and movable clevis mounted on a testing machine, each of said clevises having a centrally disposed slot for receiving said plate so that the central axis of loading passes through the centerline of said centrally disposed notch,
   a first pin carried by said fixed clevis for insertion into one of said spaced loading holes for transmitting a force thereto in one direction,
   a second pin carried by said movable clevis for insertion into the other of said spaced loading holes for transmitting a force thereto in the opposite direction thereby producing a rotational moment in said plate, and
   a third pin carried by said movable clevis for mating with said full cutout thereby arresting rotational moment.

2. Apparatus as claimed in claim 1 wherein the material of said plate is an engineering type material.

3. Apparatus as claimed in claim 2 wherein the material of said plate is aluminum.

4. Appratus as claimed in claim 1 wherein the material of said plate is a resin.

5. Apparatus as claimed in claim 1 including means for reversing the movement of said movable clevis thereby reversing the forces transmitted by said first and second pins.

6. Apparatus as claimed in claim 1 wherein the ratio of the length of the notch to the vertical distance along the notch to the top of the full cutout is between about 0.6 and 0.75.

7. Apparatus as claimed in claim 6 wherein the length of the notch and the vertical distance to the top of the full cutout are measured from the midpoint of a common centerline of the loading holes.

8. Apparatus as claimed in claim 1 including a plate mounted on the fixed clevis for sliding engagement with the edge of the movable clevis for reducing sideward movement of the apparatus resulting from the arresting of the rotational moment by the third pin.

9. Apparatus as claimed in claim 1 wherein the movable clevis has an aperture for receiving said second loading pin to rigidly mount the same for insertion into said other loading hole.

10. Apparatus as claimed in claim 1 wherein the movable clevis has an open vee-shaped notch for supporting the second loading pin.

11. An apparatus for Mode II loading a test specimen having a notch with a loading hole on each side thereof using clevises carrying pins which pass through said loading holes for transmitting a loading force from a testing machine so that the central axis of loading passes through the centerline of said notch with a resulting rotational moment in said specimen, the improvement comprising
   a full cutout in said test specimen opposite said notch, and
   a member mounted on one of said clevises for mating with said cutout thereby arresting said rotational moment.

12. Apparatus as claimed in claim 11 wherein the material of said plate is an engineering type material.

13. Apparatus as claimed in claim 12 wherein the material of said plate is aluminum.

14. Apparatus as claimed in claim 11 wherein the material of said plate is a resin.

15. Apparatus as claimed in claim 11 wherein one of said clevis is fixed and the other is movable, means for reversing the movement of said movable clevis thereby reversing the forces transmitted by said pins.

16. Apparatus as claimed in claim 15 including a plate mounted on the fixed clevis for sliding engagement with the edge of the movable clevis for reducing sideward movement of the apparatus resulting from the arresting of the material moment by said member.

17. Apparatus as claimed in claim 15 wherein the movable clevis has an aperture for receiving one of said loading pins to rigidly mount the same for insertion into one of said loading holes.

18. Apparatus as claimed in claim 15 wherein the movable clevis has an open vee-shaped notch for supporting one of the loading pins.

19. Apparatus as claimed in claim 11 wherein the ratio of the length of the notch to the vertical distance along the notch to the top of the full cutout is between about 0.6 and about 0.75.

20. Apparatus as claimed in claim 19 wherein the length of the notch and the vertical distance to the top of the full cutout are measured from the midpoint of a common centerline of the loading holes.

* * * * *

UNITED STATES PATENT AND TRADEMARK OFFICE
CERTIFICATE OF CORRECTION

PATENT NO.    : 4,916,954
DATED         : April 17, 1990
INVENTOR(S)   : Robert J. Buzzard It is certified that error appears in the above-identified patent and that said Letters Patent is hereby corrected as shown below:

Column 6, line 29, cancel "An" and insert --In--.

Signed and Sealed this

Twenty-fourth Day of December, 1991

Attest:

HARRY F. MANBECK, JR.

*Attesting Officer*  *Commissioner of Patents and Trademarks*